United States Patent

Spencer et al.

[11] Patent Number: 5,244,522
[45] Date of Patent: Sep. 14, 1993

[54] TOTAL CONTAINMENT WELDING OF PLASTIC TUBES

[75] Inventors: Dudley W. C. Spencer; Valdis Ivansons, both of Wilmington; Ivars Ivansons, Newark, all of Del.

[73] Assignee: Denco Inc., Wilmington, Del.

[21] Appl. No.: 904,589

[22] Filed: Jun. 26, 1992

Related U.S. Application Data

[63] Continuation-in-part of Ser. No. 764,249, Sep. 23, 1991, Pat. No. 5,209,800, which is a continuation-in-part of Ser. No. 682,977, Apr. 10, 1991, Pat. No. 5,156,701, which is a continuation-in-part of Ser. No. 604,979, Oct. 29, 1990, Pat. No. 5,158,630.

[51] Int. Cl.$^5$ .............................................. B32B 31/18
[52] U.S. Cl. ................................. 156/158; 156/198; 156/227; 156/251; 156/304.2; 156/304.6; 156/515; 156/518; 156/530
[58] Field of Search ................... 156/158, 304.2, 304.6, 156/251, 515, 518, 530, 198, 227

[56] References Cited

U.S. PATENT DOCUMENTS

| | | | |
|---|---|---|---|
| 3,853,655 | 12/1974 | Pecha | 156/304.6 |
| 4,753,697 | 6/1988 | Shaposka et al. | 156/304.6 |
| 4,897,138 | 1/1990 | Shaposka et al. | 156/304.2 |
| 5,141,592 | 8/1992 | Shaposka et al. | 156/158 |

*Primary Examiner*—Caleb Weston
*Attorney, Agent, or Firm*—Connolly & Hutz

[57] ABSTRACT

A pair of hollow plastic tubes are welded together by mounting each tube in the clamp jaws of a holder in a bent condition to form the U-shape. A structural element is utilized to create a space between the bight of the U-shape and the holder. The bent tubes are disposed toward each other. A tube section separating member is moved into contact with the bent tubes and through the space between each bight and its holder to create a set of two tube sections from each bent tube. A tube section from one set is aligned with a tube section from the other set and the aligned sections are welded together. The structural element may be a weld seam resulting from a prior welding.

25 Claims, 3 Drawing Sheets

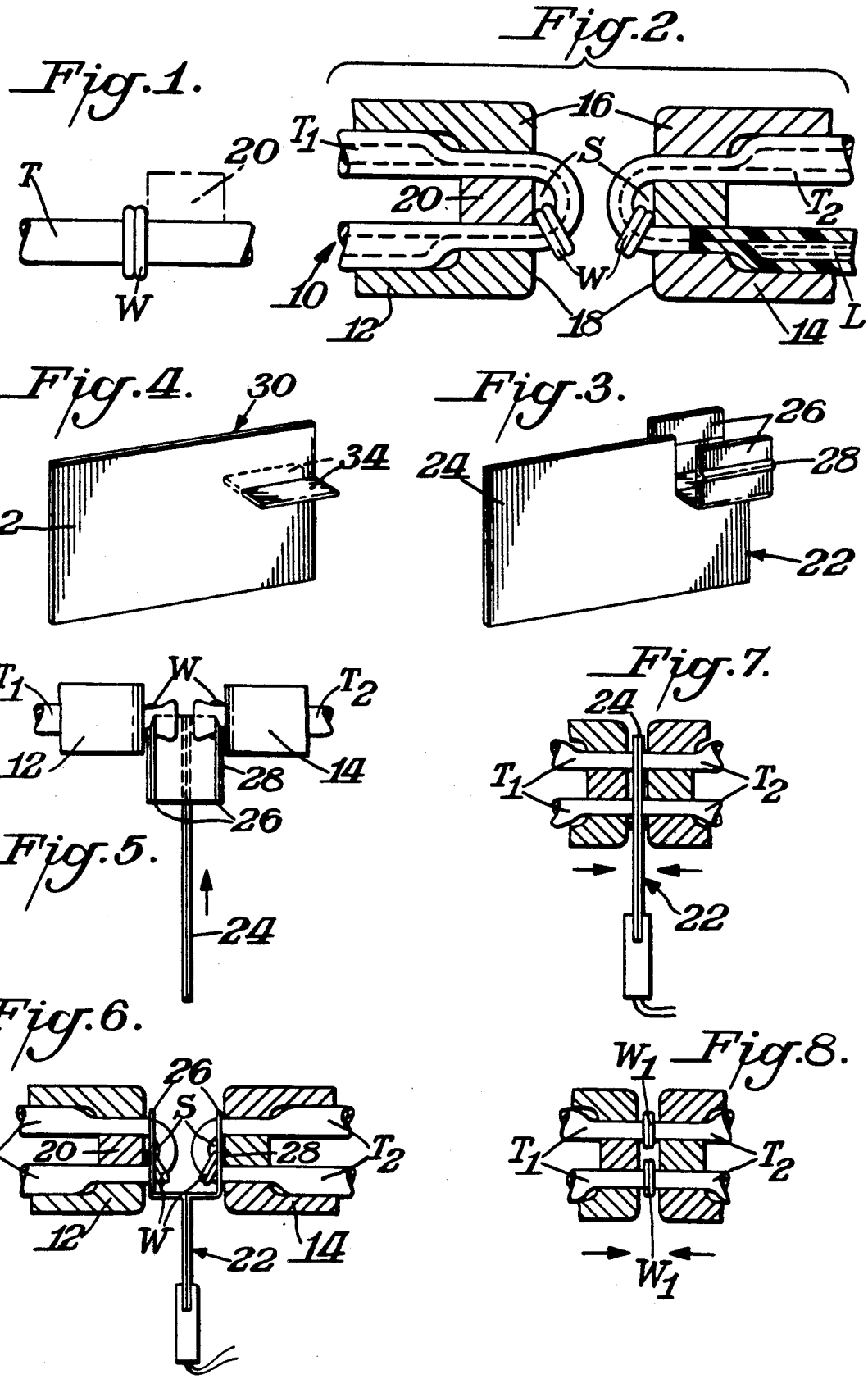

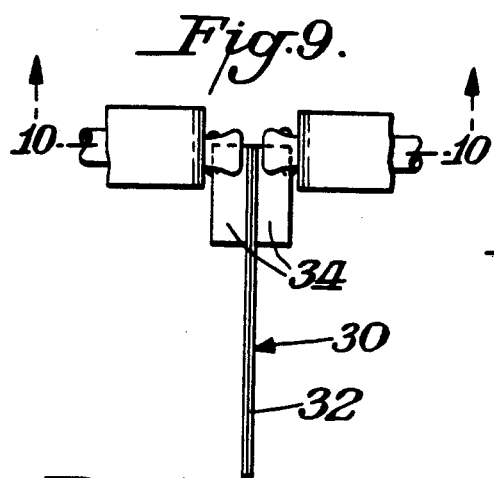
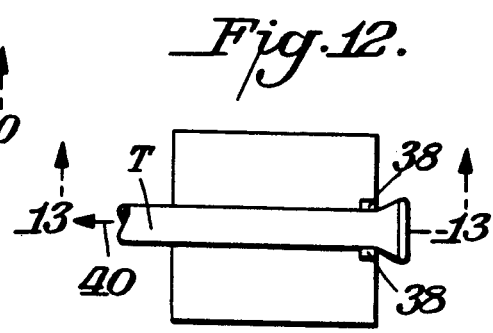
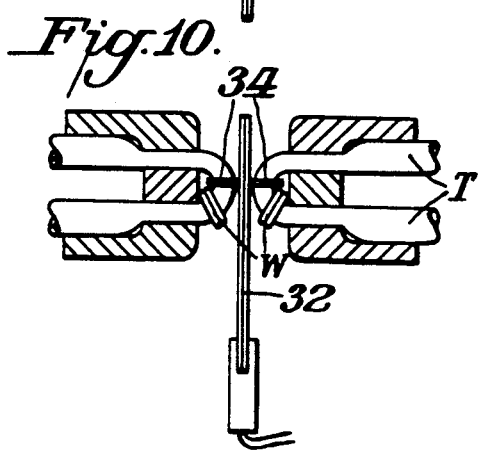
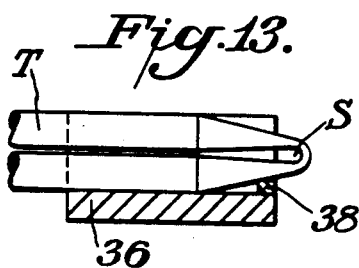
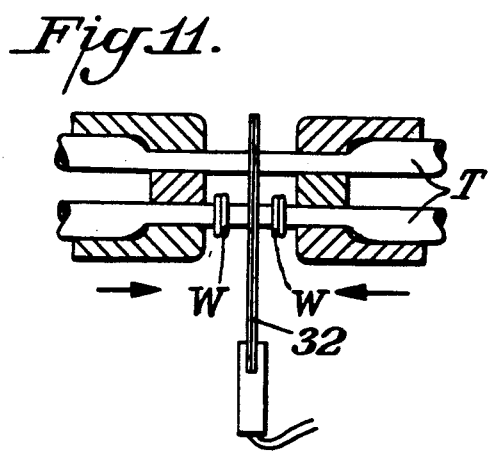
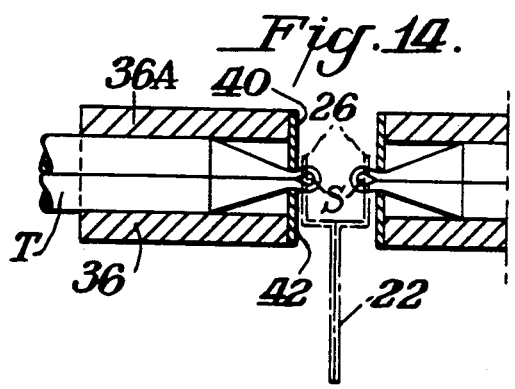

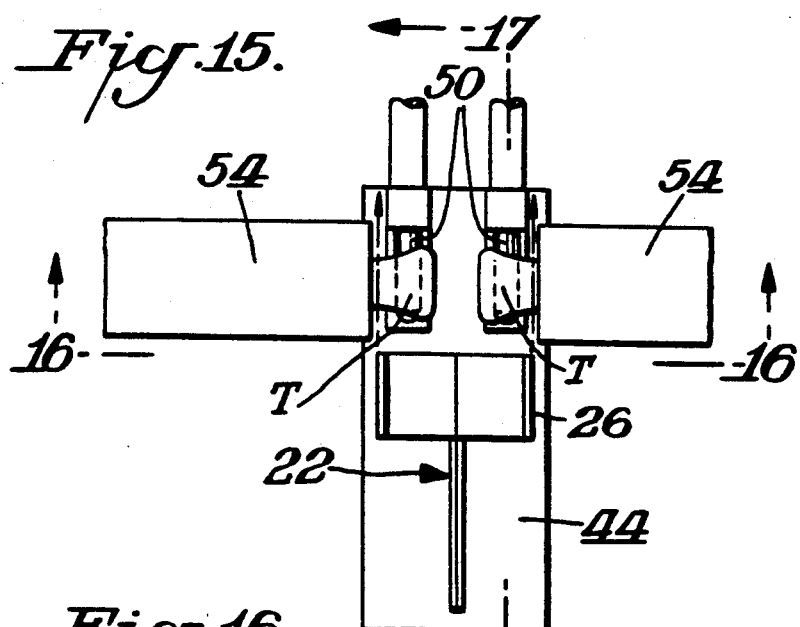
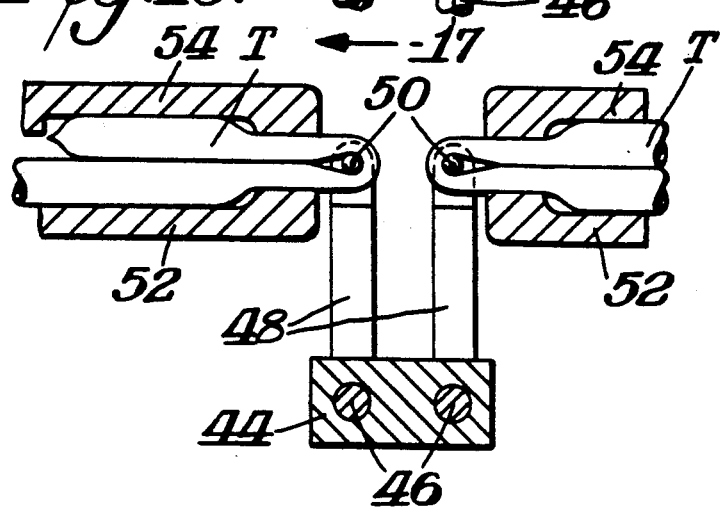
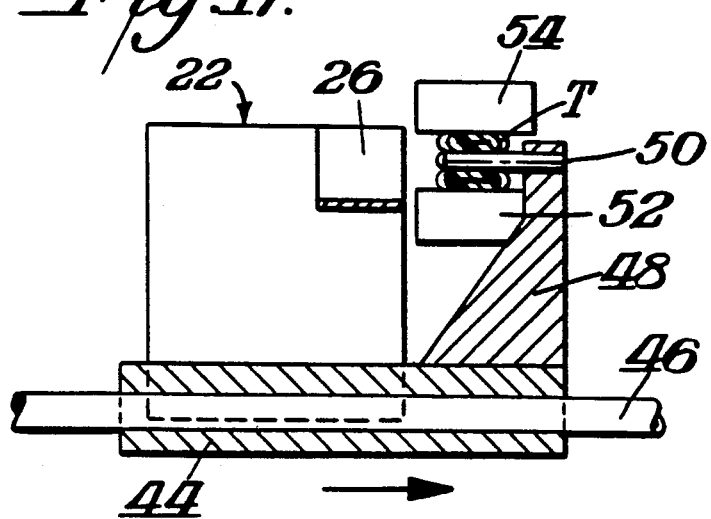

TOTAL CONTAINMENT WELDING OF PLASTIC TUBES

CROSS-REFERENCE TO RELATED APPLICATIONS

This application is a continuation-in-part of application Ser. No. 764,249 filed Sep. 23, 1991 U.S. Pat. No. 5,209,800, application Ser. No. 682,977 filed Apr. 10, 1991, U.S. Pat. No. 5,156,701 and application Ser. No. 604,979 filed Oct. 29, 1990, U.S. Pat. No. 5,158,630.

BACKGROUND OF THE INVENTION

The present invention is directed to the total containment welding of plastic tubes. Various prior art exists disclosing different approaches for welding plastic tubes together. The general approach which had been followed by the prior art was to place two tubes across a pair of holders and then cut through the tubes to form two sets of aligned tube sections. One of the sets would then be moved to realign a section from one set with a section from the other set. The realigned tubes would then be welded together.

U.S. Pat. No. 4,753,697 discloses a variation of the prior general approach. In U.S. Pat. 4,753,697 FIGS. 17-20 illustrate a technique wherein each tube in a pair of tubes is folded back toward itself to create a U-shape. A heated wafer is positioned in the space between the bent tubes. The bent tubes are then moved toward each other against the stationary heated wafer. The heated wafer melts sufficiently through the tubes to create four tube sections. The heated wafer is then removed from between the four tube sections and the aligned tube sections are welded together.

The above parent applications describe an improvement over the techniques illustrated in FIGS. 17-20 of U.S. Pat. No. 4,753,697. This improvement involves a melt/wipe process wherein there is simultaneous movement of the heated wafer through the gap between the tubes as the tubes are moved toward each other. Thus, the moving wafer melts the tubes as it wipes across them.

Parent applications Ser. No. 604,979 and Ser. No. 682,977 relate to the techniques wherein each tube is folded toward itself to form a U-shape. Parent application Ser. No. 764,249 discloses a variation of those techniques wherein there is no bending of the tube. The reason for avoiding the tube bending is the concern that in the inner portion of the bight where the tubes are bent, bacteria will exist which will not be killed during the melt/wipe process. By avoiding a bending of the tubes there is no inner bight portion where bacteria can survive.

SUMMARY OF THE INVENTION

An object of this invention is to provide techniques for the sterile or total containment welding of plastic tubes.

A further object of this invention is to provide such techniques which are particularly adaptable for use with the melt/wipe system.

A still further object of this invention is to provide a total containment welding of plastic tubes which utilizes bent tubes while effectively killing any bacteria that might otherwise be at the inner bight portion of the bent tubes.

In accordance with this invention, each tube is mounted in the clamp jaws of a holder bent toward itself to form a U-shape. A structural element is utilized to create a space between the bight of the U-shape and the holder. A tube section separating member which is preferably a heater wafer is moved into contact with the bent tubes and through the space between each bight and its holder to create a set of two tube sections from each bent tube. A tube section from one set is aligned with a tube section from the other set and the aligned tube sections are welded together.

The structural element may be the weld seam on the tube resulting from a prior welding of two tube segments welded together to form the tube. The weld seam would be disposed against the holder near the bight and act as a lever to pivot the bight away from the holder. Where the tube has no weld seam, the structural element may be a rod around which the tube is bent and then the rod is removed.

In a preferred practice of the invention the heated wafer includes a pair of offset parallel melt members which are offset from the central portion by a distance to dispose each melt member at the space between the holder and the bight. Each melt member may include an outwardly extending projection or sweep for clearing out any debris during the melt operation.

In accordance with a further embodiment of the invention the wafer has a pair of wing sections which are dimensioned to extend across the bight portion and into the space near the holder.

THE DRAWINGS

FIG. 1 illustrates a plastic tube which would be utilized with a second similar plastic tube in one practice of this invention;

FIG. 2 is a cross-sectional view in elevation of a total containment welding system in accordance with this invention for welding tubes such as shown in FIG. 1;

FIG. 3 is a perspective view of a tube section separating member in the form of a heated wafer which is usable in the practice of this invention;

FIG. 4 is a perspective view of an alternate view of tube section separating member;

FIG. 5 is a plan view showing an initial step in the method for practicing the invention using the wafer of FIG. 3 with the tubes and holders of FIG. 2;

FIG. 6 is an elevation view in section of the FIG. 5 step in the sequence of practicing the invention;

FIGS. 7-8 are elevation views in section showing still further steps in the sequence of practicing the invention;

FIG. 9 is a plan view similar to FIG. 5 showing use of the wafer of FIG. 4 in the practice of this invention;

FIG. 10 is a cross-sectional view taken through FIG. 9 along the line 10—10;

FIG. 11 is a view similar to FIG. 10 showing a further step in the practice of this invention;

FIG. 12 is a plan view showing a further alterative practice of this invention;

FIG. 13 is a cross-sectional view taken through FIG. 12 along the line 13—13;

FIG. 14 is a cross-sectional view in elevation showing a further step in the practice of the invention shown in FIGS. 12-13;

FIG. 15 is a top plan view of a total containment welding system in accordance with a further alternative practice of this invention; and FIGS. 16 and 17 are cross-sectional views taken through FIG. 15 along the lines 16—16 and 17—17, respectively.

DETAILED DESCRIPTION

The various parent applications disclose techniques for effectively welding plastic tubes together. The details of those parent applications are incorporated herein by reference thereto. Parent application Ser. No. 604,879 and parent application Ser. No. 682,977 relate to techniques utilizing a melt/wipe process wherein four tube sections are formed by melt/wiping across two bent tubes. Parent application Ser. No. 764,249 discloses a variation of the melt/wipe process which avoids the bending of the tubes and rather operates while the tubes are in a straight unbent position.

There are circumstances where the bending of tubes is desirable. For example, the bending of tubes gently expresses live cells away from the weld site. This is particularly important for a) blood and blood component protocols, b) where all liquid should be removed from the weld site to make a weld without encountering the liquid heat sink, c) a process which is totally contained in that nothing enters and nothing leaves, d) various practices of the melt/wipe process, e) a process which avoids leakages or spills by clamping the tube in the area of the bend, f) for use in all thermal plastic tube compositions, g) where it is desired to have discarded stub ends which can be retained for a sample record of enfused fluids, and h) where the stub ends are desired for providing a quantitative analysis for therapy of a patient or process.

The present invention, in general, involves techniques for forming an open area in the bight portion of the U-shaped bend where the U-shaped bend extends outwardly beyond the holders. The tubes are then severed into sections by a tube section separating member which passes through the open space. In the preferred practice of the invention the melt/wipe system is used which incorporates a heated wafer as the tube section separating member. In the preferred practice of the invention the two sets of bent tubes are automatically aligned with each other when each tube is separated into two tube sections by aligning the bent tubes before separation. Thus, each tube section is aligned with a corresponding tube section from the other tube. The invention, however may be practiced in other manners including the use of a cutting instrument as the tube section separating member rather than a heated wafer. Additionally, the bent tubes need not be initially aligned, but rather the alignment of the two sections to be joined together may be accomplished by a subsequent displacement by one or both sections after the separation has taken place as is done in the prior art.

FIGS. 1-3 and 5-8 illustrate one practice of the invention. As shown therein use is made of the fact that a tube T is in the form of a tube which had originally been two tube segments welded together to form a weld seam W having an enlarged diameter flange with respect to the diameter of the tube T. The weld seam or flange W can be shaped to control the amount of flange for subsequent welding by making small pockets in the clamp faces.

As shown in FIG. 2 an assembly 10 is provided for accomplishing the total containment welding of plastic tubes $T_1$ and $T_2$. As shown therein the assembly 10 includes a pair of holders 12,14 each of which is provided with a pair of clamp jaws 16,18. An intermediate spacer bar 20 is located between the clamp jaws. In practice a tube would be placed in a groove in its holder and bent around spacer 20. The tube would be pulled rearwardly until the flange or weld seam W is disposed in contact with the outer surface of spacer 20. This technique for the proper location of weld seam W being achieved by pacing the tube a groove and pulling the tube until the weld seam contacts the spacer 20 is schematically illustrated in FIG. 1. The tube would then be bent over spacer 20 and the clamp jaws 16,18 would be moved toward each other to create a flattened portion of the tube at its U-shaped bend with any liquid L being squeezed away from and out of the flattened portion as shown in cross-section in FIG. 2. This assures trapping bacteria and cells and forcing the cells out of the bent section where the tube is flattened by the clamp jaws. The weld seam W acts as a lever or pivot member to assure that a space S is created at the bight portion of the bent tube which extends outwardly beyond holder 12 or 14. The holders are then moved toward each other until the bent tubes barely touch as shown in FIG. 5.

In the practice of this invention utilizing the melt/wipe technique, a heated wafer is used as the tube section separating member. The wafer may take various forms including the various forms illustrated in the parent applications. FIG. 3 shows a form of wafer 22 which includes a substantially flat main portion 24 and has a pair of parallel offset portions 26 which form legs of a U at the upstream or lead end of the wafer 22 to form a melting section. The legs 26 have outward bends or bulges 28 which function as sweep elements. In practice, wafer 22 would be moved toward the bent tubes as the tubes are moving toward each other. The spacing between legs 26, 26 is such that the legs are spaced by the distance between the open spaces S,S when the legs contact the bent tubes. Because wafer 22 is a heater element the legs melt through the bent tubes and wipe the melted plastic away in the melt/wipe technique described in the parent applications. Wafer 22 continues to move in its tube section separating direction simultaneously with the holders moving toward each other to maintain proper contact of legs 26 with the tube ends. FIG. 5, for example, illustrates the initial phase of the tube section separation. FIG. 6 is an elevation view of FIG. 5 and shows the legs partially through each bent tube as they are melting through the bent tubes.

FIG. 7 illustrates the next sequence of operation after legs 26,26 have passed through the bent tubes and the resulting tube sections have been urged into contact with the main flat portion of wafer 22. As shown therein a set of two tube sections is formed from each bent tube with a section of each set being aligned with a corresponding section of the other set. By maintaining the four tube sections in contact with the flat portion 24 of heated wafer 22 the ends of the tube sections are maintained in a melted condition capable of being welded together.

FIG. 8 shows the tube sections after the trailing end of wafer 22 has completely passed through the tubes and when the holders have urged the melted ends of each tube section into contact with a corresponding aligned tube section to form weld seams $W_1$ which joins each pair of tube sections together. One of the joined pairs of tube sections could be used, for example, to connect the main portions of the tubes while the other pair of joined tube sections could produce a stub ends which could be disposed of or could be used for other purposes as previously described.

During the tube section separation by means of wafer 22 debris might result in the exposed interior of each tube section. Sweep member 28 functions to penetrate the interior and remove any such debris which would otherwise exist between the tubes.

Any suitable dimensions may be used for the U-shaped portions of wafer 22. For example, each leg 26 may be 6 mm high with sweep member 28 located centrally 3 mm from each end and projecting outwardly 1 mm. Sweep member 26 preferably has a thickness of 0.5 mm. The legs 26 would be spaced, for example, 5 mm apart. Wafer 22 itself would have a length of 28 mm and a height of 20 mm.

A further advantage of wafer 22 is that the U-shaped separating sections form a collection channel for melted material at the bight of each bent tube.

Once the pairs of tube sections have been joined together it is possible to open communication between the resultant tube by simply popping open the seal under finger pressure.

FIG. 4 illustrates an alternative form of wafer 30. As shown therein wafer 30 includes a main flat portion 32 and a pair of wings 34. FIGS. 9-10 illustrate the use of wafer 30 in the melt/wipe process for separating tube sections. As shown therein the heated wafer would melt the tube ends and the wings would penetrate into the open space S,S provided at the bight portion of each tube. Wafer 30 could operate in a manner similar to the wafer shown in parent application Ser. No. 764,246.

After the four separate tube sections have been formed pairs of tubes would be joined together in the same manner illustrated in FIG. 8.

FIG. 11 illustrates a further variation of this invention. As shown therein after the bight portion has been melted away and the tube sections are in contact with the flat portion 24 or 32 of the wafer the tube ends from the resulting four sections assume a generally perpendicular position relative to the flat portion of the wafer. The rate of movement and dimensions may be selected to insure that the exposed tube ends remain in contact with the wafer for a sufficient time so that the melting which takes place includes a melting of the weld seam W. Thus, the weld seam resulting from the prior welding operation is no longer present when the pairs of tubes are later welded together.

FIGS. 12-14 illustrate an alternative practice of this invention for forming an open space S at the bend of the tube T. As shown therein the tube is laid in the groove of holder 36. As shown in FIG. 12 holder 36 includes a pair of pegs or projections 38 disposed on each side of tube T. Tube T is then bent upon itself with the lower portion of the tube in contact with pegs 38 and with the bight of the U-shaped bend being exposed externally of holder 36 as shown in FIG. 13. Each tube is then pulled in an inward direction as indicated by the arrow 40 in FIG. 12. Upon being inwardly pulled the pegs 38 act to constrict the tube and maintain the bent portion outside of holder 36 while narrowing the thickness in the general area of the pegs 38. This narrowing of thickness creates the open space S. Thus pegs 38 function as structural elements located at the bend for creating the open space. An upper holder member 36A is then mounted to lower holder 36 and a set of thin clamp jaws 40,42 flatten tube T at the portion where tube T emerges from holder 36. As shown in FIG. 14 a wafer such a wafer 22 is then used to melt through the bent portions by having the legs 26 pass through the open space of each tube.

FIGS. 15-17 illustrates the use of pins on a carriage as the structural elements for creating the open space at the bight of the U-shaped bend in the sets of tubes. As shown therein a carriage 44 is mounted on tracks 46 for movement in a horizontal direction with respect to the horizontally oriented bent tubes T. Carriage 44 includes a pair of upstanding mounting members 48 each having a pin or rod 50 extending outwardly in a horizontal plane. Pins or rods 50 would be spaced apart by the distance where the open spaces are to be created at the bent portions of tubes T,T. In practice each tube would be placed in the groove of its respective holder 52 and then the tube would be bent around pins or rod 50 as best illustrated in FIG. 16 with each tube then being bent into contact with itself. After each tube T has been bent around its rod 50 the upper clamp jaw 54 is manipulated to flatten each tube with the bight portion extending outwardly from the holders. The physical presence of the rods 50 creates a space at the bight portion of each bent tube. Carriage 44 is then retracted to remove rods 50, thus leaving the open space where the rods had been. After carriage 44 is retracted the carriage is removed and a wafer, such as wafer 22 is used to create four separate tube sections in the manner previously described.

The various practices of this invention are advantageous in that they enable the effective use of bent tubes for obtaining a total containment welding wherein at least one pair of tube sections are connected together. The invention would be ideal for all practical size tubing from 1 mm to 100 mm with the welding apparatus sized to accommodate the particular tube diameter. The invention would be ideal for medical protocols where internal fluids such as gases, liquids or gels must be shut off for more than, for example, ten seconds.

What is claimed is:

1. A method of welding a pair of hollow plastic tubes comprising mounting each tube in clamp jaws of a holder with each tube bent upon itself to form a U-shaped bend, providing a pair of structural elements separate and distinct from the tubes, disposing each structural element transversely across a tube externally of the clamp jaws before the tube is bent, bending each tube around the structural element to create an open space at the bight of the U-shaped bend externally of the clamp jaws, removing the structural elements after the open spaces are created and the tubes are clamped, locating the holders with their bent tubes disposed toward each other, moving a tube section separating member into contact with the bent tubes and through the open space at the bight of each U-shaped bend to create a set of two tube sections from each bent tube, aligning a tube section from one set with a tube section of the other set, and welding the aligned tube sections together.

2. The method of claim 1 wherein the tube section separating member is a heated waver which melts the plastic tubes, and the holders and tubes are aligned during melting of the tubes.

3. The method of claim 2 wherein the heated waver melts the plastic tube in a melt/wipe operation.

4. The method of claim 3 wherein the heated wafer has a U-shaped upstream melting section having a pair of legs which pass through the U-shaped bend of the tubes.

5. The method of claim 4 wherein each leg includes a sweep member which clears debris out of the melted tubes.

6. The method of claim 3 wherein the wafer includes a set of aligned wings which melt through the U-shaped bends of the tubes.

7. The method of claim 1 wherein the structural element is a horizontal rod mounted to a movable carriage.

8. The method of welding a pair of hollow plastic tubes comprising providing two tubes each of which was previously formed by welding two tube sections together to form a weld seam extending outwardly of each tube at the location where the two tube sections are welded together, mounting each tube in clamp jaws of a holder with each tue bent toward itself to form a U-shaped bend, disposing the weld seam generally at the bend with a portion of the weld seam being between the rest of the tube and the clamp jaw against a structural abutment surface to create an open space at the bight of the U-shaped bend externally of the clamp jaws, locating the holders with their bent tubes disposed toward each other, moving a tube section separating member into contact with the bent tubes and through the open space at the bight of each U-shaped bend to create a set of two tube sections from each bent tube, aligning a tube section from one set with a tube section of the other set, and welding the aligned tube sections together.

9. The method of claim 8 including with its weld seam outside the holder pulling back on the tube until the weld seam contacts a spacer bar in the holder, and bending tube over the spacer bar to form the U-shaped bend.

10. The method of claim 8 wherein the tube section separating member is a heated waver which melts the plastic tubes, and the holders and tubes are aligned during melting of the tubes.

11. The method of claim 10 wherein the wafer is maintained in contact with the tube sections a sufficient time to melt the weld seam.

12. The method of claim 10 wherein the heated wafer melts the plastic tube in a melt/wipe operation.

13. The method of claim 12 wherein the heated wafer has a U-shaped upstream melting section having a pair of legs which pass through the U-shaped bend of the tubes.

14. The method of claim 13 wherein each leg includes a sweep member which clears debris out of the melted tubes.

15. The method of claim 13 wherein the wafer includes a set of aligned wings which melt through the U-shaped bends of the tubes.

16. A method of welding a pair of hollow plastic tubes comprising mounting each tube in clamp jaws of a holder with each tube bent upon itself to form a U-shaped bend externally of the clamp jaws, disposing a portion of the bent tube against a peg in the holder, pulling the tube inwardly against the peg so that the peg constricts the tube to narrow its thickness and maintain an open space at the bight of the U-shaped bend externally of the clamp jaws, locating the holders with their bent tubes disposed toward each other, moving a tube section separating member into contact with the bent tubes and through the open space at the bight of each U-shaped bend to create a set of two tube sections from each bent tube, aligning a tube section from one set with a tube section of the other set, and welding the aligned tube sections together.

17. The method of claim 16 wherein the holder is a lower holder, disposing the portion of the tube between and against two spaced pegs in the lower holder, moving an upper holder clamp jaw downwardly against each bent tube, and clamping each bent tube at its narrowed thickness.

18. The method of claim 17 wherein the tube section separating member is a heated wafer which melts the plastic tubes, and the holders and tubes are aligned during melting of the tubes.

19. The method of claim 18 wherein the heated wafer melts the plastic tube in a melt/wipe operation.

20. The method of claim 19 wherein the heated wafer has a U-shaped upstream melting section having a pair of legs which pass through the U-shaped bend of the tubes.

21. The method of claim 20 wherein each leg includes a sweep member which clears debris out of the melted tubes.

22. The method of claim 20 wherein the wafer includes a set of aligned wings which melt through the U-shaped bends of the tubes.

23. A wafer for use in welding a pair of hollow plastic tubes, said wafer comprising a heated member having a lead end and a trailing end, said heated member having a flat main portion, a U-shaped separating portion extending outwardly from said flat main portion at said lead end, and said U-shaped separating portion including a pair of parallel legs extending outwardly from said main portion.

24. The wafer of claim 23 including a sweep element extending outwardly from each of said legs.

25. The wafer of claim 24 wherein said sweep element is located centrally across its respective leg.

* * * * *